US006548629B2

(12) United States Patent
Kilgour et al.

(10) Patent No.: US 6,548,629 B2
(45) Date of Patent: Apr. 15, 2003

(54) POLAR SOLVENT COMPATIBLE POLYETHERSILOXANE ELASTOMERS

(75) Inventors: John A. Kilgour, Clifton Park, NY (US); Atchara Chaiyawat, Ballston Lake, NY (US); An-Li Kuo, Chappaqua, NY (US); Donald E. Firstenberg, Ballston Spa, NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/971,426

(22) Filed: Oct. 5, 2001

(65) Prior Publication Data

US 2002/0128375 A1 Sep. 12, 2002

Related U.S. Application Data

(62) Division of application No. 09/649,734, filed on Aug. 28, 2000, now Pat. No. 6,346,583.
(60) Provisional application No. 60/150,649, filed on Aug. 25, 1999.

(51) Int. Cl.⁷ .................................................. C08F 6/00
(52) U.S. Cl. ..................... 528/502 F; 528/35; 525/474; 525/478; 568/673; 524/588
(58) Field of Search ................... 528/35, 502 F; 525/474, 478; 568/673; 524/588

(56) References Cited

U.S. PATENT DOCUMENTS

| 2,823,218 | A | 2/1958 | Speier et al. |
|---|---|---|---|
| 3,159,601 | A | 12/1964 | Ashby |
| 3,159,662 | A | 12/1964 | Ashby |
| 3,775,452 | A | 11/1973 | Karstedt |
| 4,857,583 | A | 8/1989 | Austin et al. |
| 4,877,854 | A | 10/1989 | Hattori et al. |
| 5,138,009 | A | 8/1992 | Inoue |
| 5,191,103 | A | 3/1993 | Mehta et al. |
| 5,236,986 | A | 8/1993 | Sakuta |
| 5,276,087 | A | 1/1994 | Fujiki et al. |
| 5,412,004 | A | 5/1995 | Tachibana et al. |
| 5,506,289 | A | 4/1996 | McDermott et al. |
| 5,529,837 | A | 6/1996 | Fujiki et al. |
| 5,571,853 | A | 11/1996 | Ikeno et al. |
| 5,674,966 | A | 10/1997 | McDermott et al. |
| 5,698,654 | A | 12/1997 | Nye et al. |
| 5,717,010 | A | 2/1998 | Ward et al. |
| 5,760,116 | A | 6/1998 | Kilgour et al. |
| 5,811,487 | A | 9/1998 | Schulz, Jr. et al. |

FOREIGN PATENT DOCUMENTS

| EP | 0 848 029 | 6/1998 |
|---|---|---|
| EP | 0 885 932 | 12/1998 |
| EP | 0 934 959 | 8/1999 |

*Primary Examiner*—Robert Dawson
*Assistant Examiner*—Kuo-Liang Peng
(74) *Attorney, Agent, or Firm*—Kenneth S. Wheelock

(57) ABSTRACT

The cross-linked hydrosilylation reaction product of an alkenyl functional silicone compound, a silylhydride functional silicone compound, and one or more allyl started, hydrogen, alkyl, aryl or acyl terminated polyether compounds exhibits stability, compatibility with polar organic solvents and is useful as a component in personal care compositions.

4 Claims, No Drawings

US 6,548,629 B2

POLAR SOLVENT COMPATIBLE POLYETHERSILOXANE ELASTOMERS

CROSS-REFERENCE TO RELATED APPLICATIONS

This is a divisional of co-pending application Ser. No. 09/649,734 filed on Aug. 28, 2000, now U.S. Pat. No. 6,346,583 which is incorporated herein by reference and this applicaton claims rights of priority from U.S. Provisional Patent Application Ser. No. 60/150,649, filed Aug 25, 1999.

FIELD OF THE INVENTION

The present invention relates to silicone polymers, more specifically to polyether substituted silicone elastomers.

BACKGROUND OF THE INVENTION

The personal care industry thrives on being able to deliver multiple performance products based on a mixture of several components, each having performance characteristics important to the final formulation. One need in preparing these formulations is for materials that can both enhance performance as well as compatibilize and hold together in the formulation the various components of the formulation.

Recent technology has produced several crosslinked polydimethylsiloxane elastomers that are capable of absorbing cyclic and low molecular weight silicones useful in the personal care industry. The use of alpha-omega diallyl terminated polyethers as a chain extending component in making crosslinked siloxane elastomers has been shown (see, for example, U.S. Pat. Nos. 5,138,009; 5,412,004; 5,236,986). In one variation, these products suffer from the need to synthesize polyethers with an allyl functional group at both ends, and this is expensive because it requires a separate synthesis step to add the second allyl functional group. In addition, since the diallylpolyether is used as a chain extender, the amount that can be added to the composition is severely restricted by the need to form a polymer network. In a second variation, a polyether/hydrido substituted siloxane prepared in a separate, difficult and expensive reaction is used to introduce the polyether functionality. The present invention employs the use of a single vessel reaction to produce a uniquely structured elastomer and the polyether functionality is introduced using commercially available allyl started polyether compounds.

The synthesis of organically crosslinked siloxane elastomers that have been substituted with mono and diallyl terminated polyethers has been demonstrated (see, for example, U.S. Pat. Nos. 5,889,108; 5,811,487). These elastomers suffer from the requirement of having an alpha, omega-diolefin as the chain extender and a diffuse silylhydride crosslinker. This creates a different structure which may lose some of the desirable siloxane properties. Such organically crosslinked polymeric siloxanes appear to have significantly less absorbing efficiency relative to all siloxane based elastomers utilizing a higher functionality crosslinker.

A curable composition comprised of a branched, allyl-functional polyether, a branched, hydridosiloxy terminated polyether and a catalyst has also been disclosed (see, for example, U.S. Pat. No. 4,877,854). This composition requires difficult to make branched and allyl functional polyethers which determine the crosslink density, leaving no capability to control the amount of polyether content. The second component (siloxane) is equally difficult and expensive to make and ultimately limiting in the design flexibility to control performance. This system for making dental impressions forms a solid plastic unsuitable for making the small particle size required for personal care applications.

The structures defined in the above referenced patents are highly hydrophilic as a result of the total methyl substitution on silicone. Because of the hydrophilic nature, they are at best compatible with selected non-polar organic and siloxane based materials. This is a limiting feature as many formulated compositions useful in the personal care industry include water, polar organic materials such as low molecular weight alcohols, or a combination of both.

What is needed is a crosslinked siloxane elastomer which is efficient in absorbing low molecular weight silicones, has a pleasant feel and can be compatibilized or emulsified with water, polar organic materials, or a combination thereof.

SUMMARY OF THE INVENTION

In a first aspect, the present invention is directed to a cross-linked polyether substituted silicone elastomer, comprising the cross-linked hydrosilylation reaction product of:
 (i) an alkenyl functional silicone compound;
 (ii) a silylhydride functional siloxane; and
 (iii) an allyl started, hydrogen, alkyl, aryl or acyl terminated polyether compound.

The silicone elastomer is hydrolytically stable, in that the polyether substituents are attached to the elastomer via Si—C bonds having good hydrolytic stability and can be easily and economically prepared in a single step. As used herein, the terminology "hydrolytically stable" means a tendency not to undergo changes in structure, such as, for example, cleavage of bonds, as a result of exposure to moisture.

Preferably, the silylhydride functional siloxane contain a sufficient number of Si—H groups to hydrosilylate the desired amount of allyl terminated polyether molecules with at least 1.5 SiH groups per molecule remaining for crosslinking with the alkenyl functional silicone compound.

Preferably, the alkenyl functional silicone compound contain at least 1.5 alkenyl units per molecule and has alkenyl substitutions on any or all of the M, D or T units. The number of available functional units on the SiH and alkenyl functional sites must be sufficient to form a gel on polymerization in a volatile siloxane.

This invention makes use of allyl started polyethers that may be commercially available and made without a second addition step. Since they are monofunctional, they can be flexibly introduced into the crosslinked siloxane elastomer while retaining the polymer network structure.

In a second aspect, the present invention is directed to a method for making a cross-linked polyether substituted silicone elastomer, comprising forming the hydrosilylation reaction product of:
 (i) an alkenyl functional silicone compound;
 (ii) a silylhydride functional siloxane; and
 (iii) an allyl started, hydrogen, alkyl, aryl or acyl terminated polyether compound.

In a third aspect, the present invention is directed to a silicone composition, comprising a liquid medium, said liquid medium comprising an organic liquid, a silicone fluid or a mixture thereof; and a silicone elastomer of the present invention dispersed in the liquid medium. The elastomer of the present invention exhibits improved compatibility with organic liquids. As used herein, the "compatibility" of an elastomer with a liquid refers to the ability to form a stable dispersion of the elastomer in an organic liquid.

In a fourth aspect, the present invention is directed to an emulsion comprising an emulsion of a first liquid phase and a second liquid phase and a silicone elastomer of the present invention dispersed in the emulsion.

In a fifth aspect, the present invention is directed to a personal care composition comprising a silicone elastomer of the present invention.

DETAILED DESCRIPTION OF THE INVENTION

Silicone Elastomer

In preferred embodiment, the cross-linked alkyl substituted silicone elastomer of the present invention comprises the cross-linked hydrosilylation reaction product of, based on 100 parts by weight ("pbw") of the combined alkenyl functional silicone compound, silylhydride functional silicone compound and allyl started, hydrogen, alkyl, aryl or acyl terminated polyether compound, from 10 pbw to 99.9 pbw, more preferably from 40 pbw to 99.5 pbw, even more preferably from 65 pbw to 95 pbw of the combined alkenyl functional silicone compound and silylhydride functional silicone compound and from greater than 0.1 pbw to 90 pbw, more preferably from 0.5 pbw to 60 pbw, even more preferably from 5 pbw to 35 pbw of the one or more an allyl started, hydrogen, alkyl, aryl or acyl terminated polyether compounds.

In a preferred embodiment, the polyether substituted silicone elastomer of the present invention forms a cross-linked three dimensional network that does not dissolve in, but is capable of being swollen by a suitable liquid medium, such as for example, a low molecular weight silicone or an organic liquid. The amount of crosslinking present in the cross-linked silicone elastomer network may be characterized with respect to the degree of swelling exhibited by the network in the liquid medium. In a preferred In a preferred embodiment the alkenyl functional silicone compound comprises one or more compounds of the formula (I):

$$M_a M^{vi}_b D_c D^{vi}_d T_e T^{vi}_f Q_g \qquad (I)$$

wherein:

M is $R^1R^2R^3SiO_{1/2}$;

$M^{vi}$ is $R^4R^5R^6SiO_{1/2}$;

D is $R^7R^8SiO_{2/2}$;

$D^{vi}$ is $R^9R^{10}SiO_{2/2}$;

T is $R^{11}SiO_{3/2}$;

$T^{vi}$ is $R^{12}SiO_{3/2}$; and

Q is $SiO_{4/2}$;

$R^1$, $R^2$, $R^3$, $R^7$, $R^8$ and $R^{11}$ are each independently alkyl, preferably ($C_1$–$C_{60}$)alkyl, aryl or aralkyl;

$R^4$, $R^9$ and $R^{12}$ are each independently monovalent terminally unsaturated hydrocarbon radicals;

$R^5$, $R^6$ and $R^{10}$ are each independently monovalent terminally unsaturated hydrocarbon radicals, alkyl, aryl or aralkyl, preferably ($C_1$–$C_{60}$)alkyl, aryl or aralkyl, more preferably ($C_1$–$C_{60}$)alkyl;

a, b, c, d, e, f and g are each integers wherein:
  a, b, e, f, and g are each greater than or equal to 0 and less than or equal to 50, $0 \leq c \leq 2000$,
  $0 \leq d \leq 200$, and provided that:
  $(a+b) \leq (2+3e+3f+4g)$ and
  $1.5 \leq (b+d+f) \leq 200$.

In a highly preferred embodiment, $R^4$ is a monovalent terminally unsaturated ($C_2$–$C_6$)hydrocarbon radical; $R^5_1$, $R^6$, $R^7$ and $R^8$ are each independently ($C_1$–$C_6$)alkyl; $R^5$, $R^6$, $R^7$ and $R^8$ are each independently ($C_1$–$C_6$)alkyl; b is 2; $100 \leq c \leq 2000$; and a, d, e, f and g are each 0.

In a preferred embodiment, the silylhydride functional silicone compound comprises one or more compounds of the formula (II):

$$M_h M^H_i D_j D^H_k T_l T^H_m Q_n \qquad (II)$$

M, D, T and Q are each defined as above $M^H$ is $R^{13}R^{14}R^{15}SiO_{1/2}$;

$D^H$ is $R^{16}R^{17}SiO_{2/2}$;

$T^H$ is $R^{18}SiO_{3/2}$;

$R^1$, $R^2$, $R^3$, $R^7$, $R^8$ and $R^{11}$ are each independently alkyl, aryl or aralkyl;

$R^{13}$, $R^{16}$ and $R^{18}$ are each independently H;

$R^{14}$, $R^{15}$ and $R^{17}$ are each independently H, alkyl, aryl or aralkyl, preferably ($C_1$–$C_{60}$)alkyl, aryl or aralkyl, more preferably ($C_1$–$C_{60}$)alkyl; and h, i, j, k, l, m, and n are each integers wherein:
  h, i, l, m and n are each greater than or equal to 0 and less than or equal to 50, $0 \leq j \leq 2000$,
  $0 \leq k \leq 200$, and provided that:
  $(h+i) \leq (2+3l+3m+4n)$ and
  $1.5 \leq (i+k+m) \leq 200$.

In a highly preferred embodiment, $R^{14}$ and $R^{15}$ are each independently ($C_1$–$C_6$)alkyl, and more preferably are each methyl; $R^{13}$ is H; $4 \leq i \leq 30$; $1 \leq n \leq 15$ and h, j, k, l and m are each 0.

In an alternative highly preferred embodiment, $R^{14}$, $R^{15}$ and $R^{17}$ are each independently ($C_1$–$C_{12}$)alkyl, $R^{13}$ and $R^{16}$ are each H; $h+i=2$, $0 \leq j \leq 100$, $2 \leq k \leq 100$ and l, m and n are each 0.

In a preferred embodiment, the allyl started, hydrogen, alkyl, aryl or acyl terminated polyether compound is a polyoxyalkylene compound comprising one or more compounds of the formula (III):

$$CH_2=CH(CH_2)_oO(C_pH_{2p}O)_q(C_rH_{2r}O)_sR^{19} \qquad (III)$$

$R^{19}$ is hydrogen, alkyl, aryl or acyl, preferably ($C_1$–$C_{20}$) alkyl, aryl or acyl;

o, p, q, r and s are each integers wherein:
  $0 \leq o \leq 6$; p and r are each independently greater than or equal to 1 and less than or equal to 4; q and s are each independently greater than or equal to 0 and less than 200 such that $0 \leq q+s \leq 200$.

Suitable monovalent terminally unsaturated hydrocarbon radicals include monovalent linear or branched terminally unsaturated hydrocarbon groups. In a preferred embodiment, the terminally unsaturated hydrocarbon radicals are selected from linear or branched terminally unsaturated alkenyl groups containing from 2 to 10 carbon atoms per group, such as, for example, ethenyl, 2-propenyl, 1-methylethenyl, 2-methyl-2-propenyl, ethenylphenyl, 3-butenyl, and 7-octenyl, more preferably, ethenyl, and 2-propenyl.

Suitable monovalent alkyl groups include linear or branched alkyl groups. In a preferred embodiment, monovalent alkyl groups are selected from linear or branched alkyl groups containing from 1 to 60 carbons per group, such as, for example, methyl, ethyl, propyl, iso-propyl, n-butyl, iso-butyl, sec-butyl, tert-butyl, pentyl, hexyl, heptyl, decyl, dodecyl, stearyl, cetyl, eicosyl, tridecyl, and hexadecyl.

As used herein, the term "aryl" means a monovalent unsaturated hydrocarbon ring system containing one or more aromatic rings per group, which may optionally be substituted on the one or more aromatic rings with one or more alkyl groups, each preferably containing from 2 to 6 carbon atoms per alkyl group and which, in the case of two or more rings, may be fused rings. Suitable monovalent aromatic hydrocarbon radicals include, for example, phenyl, tolyl, 2,4,6-trimethylphenyl, 2-isopropylmethylphenyl, 1-pentalenyl, naphthyl, and anthryl.

As used herein, the term "acyl" is defined as RC=O, where R is an alkyl or aryl group as previously defined. Suitable acyl groups include, for example, acetyl and benzoyl.

Aralkyl includes, for example, phenylethyl and 2-(1-naphthyl)ethyl.

In a preferred embodiment, the silicone elastomer of the present invention is made by contacting one or more alkenyl functional silicone compounds according to formula (I) with one or more silylhydride functional silicone compounds according to structural formula (II) and one or more polyether compounds according to structural formula (III) under hydrosilylation conditions.

As used herein, the terminology "$(C_x–C_y)$", wherein x and y are each integers, in reference to an organic compound or substituent group means that the compound or group contains from x to y carbon atoms per molecule of the compound or per group. As used herein, the terminology "each independently selected from" in reference to organic substituents on an organosiloxane repeating unit of a polyorganosiloxane polymer means that each substituent group is selected independently from other substituent groups on the repeating unit and independently from the substituent groups on any other analogous repeating units of the polymer. A polyorganosiloxane polymer described herein as including more than one of a particular type of organosiloxane repeating unit, for example, diorganosiloxane ("D") units, wherein the substituents on the units are "each independently selected" from a defined group includes both polyorganosiloxane homopolymers, that is, wherein the substituents on each of the organosiloxane repeating units of the polymer are the same substituents, such as, for example, a polydimethylsiloxane polymer, as well as polyorganosiloxane copolymers, that is, a polymer containing two or more analogous organosiloxane repeating units, each bearing different substituents, such as, for example, a poly (dimethylsiloxane/methylphenylsiloxane) copolymer.

In a highly preferred embodiment, $R^4$ is a monovalent terminally unsaturated $(C_2–C_6)$hydrocarbon radical, more preferably, ethenyl or 2-propenyl, more preferably ethenyl; $R^5, R^6, R^7, R^8, R^{14}$ and $R^{15}$ are each independently $(C_1–C_6)$ alkyl, and more preferably are each methyl; $R^{13}$ is H; b is 2; $100 \leq c \leq 2000$; preferably $500 \leq c \leq 1500$; $4 \leq i \leq 30$; $1 \leq n \leq 15$ and a, d, e f, g, h, j, k, l and m are each 0.

In an alternative highly preferred embodiment, $R^4$ is a monovalent terminally unsaturated $(C_2–C_6)$hydrocarbon radical, more preferably, ethenyl or 2-propenyl, more preferably ethenyl; $R^1, R^2, R^3, R^5, R^6, R^7 R^8, R^{14}, R^{15} R^{17}$ are each independently $(C_1–C_{60})$alkyl, more preferably $(C_1–C_{12})$alkyl, still more preferably methyl, $R^{13}$ and $R^{16}$ are each H; b is 2; $100 \leq c \leq 2000$; preferably $500 \leq c \leq 1500$; h+i=2,$0 \leq j \leq 100$, $2 \leq k \leq 100$ and a, d, e, f, g, l, m and n are each 0.

Suitable alkenyl functional silicone compounds and silylhydride functional silicone compounds are described in, for example, U.S. Pat. Nos. 5,506,289; 5,674,966; 5,717,010; 5,571,853; and 5,529,837, the disclosures of which are each hereby incorporated by reference herein. The alkenyl functionality and the silylhydride functionality may be combined into one self-curing molecule or compound, such as, for example, as disclosed in U.S. Pat. No. 5,698,654.

In a preferred embodiment, the hydrosilylation reaction is carried out in the presence of a hydrosilylation catalyst.

Suitable catalysts are known, as described in, for example, U.S. Pat. Nos. 2,823,218; 3,159,601; 3,159,662; and 3,775,452, and include, for example, ruthenium, osmium, rhodium, iridium, palladium and platinum hydrosilylation catalysts.

In a preferred embodiment, the hydrosilylation reaction is carried out in a reaction medium comprising one or more silicone fluids, one or more or organic liquids, each as more fully described below, or a mixture thereof.

Processing

The crosslinked silicone elastomer of the present invention may then be further swollen with additional solvent, which may be either the same as or different from the reaction medium used in making the crosslinked silicone polymer. The swollen crosslinked silicone elastomer is then subjected to shear force, for example, using a two-roll mill, a homogenizer or a high shear mixer, to break the elastomer into small particles.

In a preferred embodiment, the swollen silicone elastomer is subjected high flow induced shear by forcing the elastomer through an orifice at high pressure. In a preferred embodiment, the viscosity of the swollen elastomer should be greater than 500 centiStokes ("cStk"), more preferably greater than 750 cStk, still more preferably greater than 1000 cStk and most preferably over 5000 cStk. The orifice size is limited by the ability of the pumping system to maintain sufficient pressure. In a preferred embodiment, the orifice area is less than 0.5 square inches ("in$^2$"), preferably less than 0.1 in$^2$, more preferably less than 0.05 in$^2$, and most preferably less than 0.01 in$^2$. In a preferred embodiment, the pressure is above 500 pounds per square inch ("psi"), more preferably above 1000 psi, still more preferably, over 1500 psi and most preferably over 2000 psi.

Silicone Compositions

In a preferred embodiment, the silicone composition of the present invention comprises, based on 100 pbw of the composition, from 1 pbw to 99 pbw, more preferably from 5 pbw to 95 pbw, and even more preferably 10 pbw to 90 pbw of the liquid medium, from 1 pbw to 99 pbw, more preferably from 5 pbw to 95 pbw, and even more preferably 10 pbw to 90 pbw of the silicone particles.

In a preferred embodiment, the liquid medium consists essentially of an organic liquid. In an first alternative preferred embodiment, the liquid medium consists of a silicone fluid. In a second alternative preferred embodiment, the liquid medium comprises an organic liquid, and a silicone fluid that is miscible with the organic liquid.

Silicone Emulsions

In a preferred embodiment, the silicone emulsion of the present invention comprises, based on 100 pbw of the combined amount of the first and second liquids, from 0.1 pbw to 99.1 pbw, more preferably from 5 pbw to 95 pbw and even more preferably from 15 pbw to 85 pbw, of the first liquid and from 0.1 pbw to 99.1 pbw, more preferably from 5 pbw to 95 pbw and even more preferably from 15 pbw to 80 pbw, of the second liquid and, based on 100 pbw of the silicone emulsion, from 0.001 pbw to 75 pbw, more preferably from 0.1 pbw to 40 pbw and even more preferably from 0.5 pbw to 20 pbw, of the silicone elastomer of the present invention.

In a first highly preferred embodiment of the silicone emulsion of the present invention, the first liquid phase is a continuous phase and the second liquid phase is a discontinuous phase emulsified with the continuous first liquid phase. In an alternative highly preferred embodiment of the silicone emulsion of the present invention, the second liquid phase is a continuous phase and the first liquid phase is a discontinuous phase emulsified with the continuous second liquid phase.

In a preferred embodiment, the first liquid comprises a silicone fluid, an organic liquid, or a mixture thereof and the second liquid comprises water, a substantially polar organic liquid or a mixture thereof. In a preferred embodiment, no emulsifying agent is necessary to form a stable emulsion.

Optionally, the silicone emulsion of the present invention may further comprise one or more emulsifying agents. Suitable emulsifying agents useful in preparing the emulsions of the present include, for example, silicone-containing emulsifying agents, emulsifying agents derived from sorbitan compounds and emulsifying agents derived from fatty alcohols, more preferably the emulsifying agent is selected from the group consisting of fatty acid esters, sorbitan sesquioleate, sorbitan oleate, sorbitan isostearate, polyglyceryl-3 oleate, alkoxylated alcohols such as laureth-4, laureth-7, deceth-12, steareth-10, hydroxylated or alkoxylated derivatives of silicone compounds such as dimethicone copolyol, cetyl dimethicone copolyol, and lauryl methicone copolyol, glyceryl esters such as polyglyceryl4-isostearyl and mixtures thereof; and most preferably the emulsifying agent is dimethicone coployol which may or may not be dispersed in a silicone oil or cyclomethicone diluent.

The first liquid, second liquid and silicone elastomer are mixed together to form the silicone emulsion of the present invention. Preferably, the components of the disperse phase are added to the components of the continuous phase while subjecting the mixture of components to low shear mixing and the mixture so formed is then subjected to high shear mixing. In a preferred embodiment, a dispersion of the silicone elastomer of the present invention in the first liquid is slowly added to the second liquid while subjecting the combined phases to low shear mixing, such as, for example, in a mixing tank equipped with a propeller-type stirrer, and then the mixture so formed is subjected to high shear mixing, for example, in a Sonolator® apparatus, a Gaulin® homogenizer or other high shear mixer, such as an Eppenbach Mixer, to form the silicone emulsion. In a more highly preferred embodiment, an emulsifying agent is combined with the first liquid prior to adding the components of the first phase to the components of the second phase.

Silicone Fluid

Silicone fluids suitable for use as the silicone fluid component of the composition of the present invention are those organosilicon compounds that are in the liquid state at or near room temperature, for example, from about 20° C. about 50° C., and about one atmosphere pressure. In a preferred embodiment, the silicone fluid component of the composition of the present invention having a viscosity of below about 1,000 centistokes, preferably below about 500 centistokes, more preferably below about 250 centistokes, and most preferably below 100 centistokes, at 25° C. Suitable silicone fluids include, for example, cyclic silicones of the formula $D_z$, wherein D is defined as above, $R^7$ and $R^8$ are each preferably methyl, and z is an integer wherein $3 \leq z \leq 12$, such as, for example, hexamethylcyclotrisiloxane ("$D_3$"), octamethylcyclotetrasiloxane ("$D_4$"), decamethylcyclopentasiloxane ("$D_5$"), and dodecamethylcyclohexasiloxane ("$D_6$") as well as linear organopolysiloxanes having the formula (IV):

$$M'D'_wM' \quad \text{(IV)}$$

wherein:

M' is $R^{20}R^{21}R^{22}SiO_{1/2}$;

D' is $R^{23}R^{24}SiO_{2/2}$;

$R^{20}$, $R^{21}$, $R^{22}$, $R^{23}$ and $R^{24}$ are each independently alkyl, aryl or aralkyl;

w is an integer of from 0 to 300, wherein $0 \leq w \leq 300$, preferably $0 \leq w \leq 100$, more preferably $0 \leq w \leq 50$, and most preferably $0 \leq w \leq 20$.

Organic Liquid

Suitable organic liquids include any organic compound that is in the liquid state at or near room temperature, for example, from about 20° C. about 50° C., and about one atmosphere pressure, that is substantially inert to the silicone phase, that is, does not undergo a chemical reaction with any of the components of the silicone phase, under the anticipated conditions of processing and use and that is suitable for use in the intended end-use application, such as, for example, a cosmetic composition, to be prepared from the non-aqueous silicone composition of the present invention.

As used herein, the terminology "substantially polar" means exhibiting a dipole moment of from about 0.9 to 4.5. Suitable substantially polar organic liquids include water and organic hydroxylic liquids, such as, for example, alcohols, glycols, polyhydric alcohols and polymeric glycols. More preferably, the substantially polar organic liquid is selected from of alcohols including polyhydric alcohols, glycols, including polymeric glycols, and mixtures thereof. Preferably, the substantially polar organic liquid contains an $(C_1-C_{12})$alcohol, such as for example, ethanol, propyl alcohol and iso-propyl alcohol, a $(C_2-C_{12})$glycol, such as for example, ethylene glycol, propylene glycol, dipropylene glycol, tripropylene glycol, butylene glycol, iso-butylene glycol and methyl propane diol, a polyhydric alcohol, such as for example, glycerin erythritol and sorbitol, or a polymeric glycol, such as for example, polyethylene glycol, polypropylene glycol mono alkyl ethers and polyoxyalkylene copolymers. In a highly preferred embodiment, the substantially polar organic liquid is selected from ethanol, propyl alcohol, iso-propyl alcohol, ethylene glycol, propylene glycol, dipropylene glycol, tripropylene glycol, butylene glycol, iso-butylene glycol, methyl propane diol, glycerin, erythritol sorbitol, polyethylene glycol, polypropylene glycol mono alkyl ethers, and polyoxyalkylene copolymers.

Personal Care Compositions

The personal care applications where the silicone elastomer of the present invention may be employed include, but are not limited to, deodorants, antiperspirants, skin lotions, moisturizers, hair care products such as shampoos, mousses and styling gels, protective creams such as sunscreen and anti-aging products, color cosmetics such as lipsticks, foundations, blushes, makeup, and mascaras and other cosmetic formulations where silicone components have conventionally been added, as well as drug delivery systems for topical application of medicinal compositions that are to be applied to the skin.

Suitable personal care compositions are made by combining, in a manner known in the art, such as, for example, by mixing, one or more of the above components with the silicone elastomer of the present invention, the silicone composition of the present invention or the silicone emulsion of the present invention. Suitable personal care compositions may be in the form of a single phase or in the form of an emulsion, including oil-in-water, water-in-oil and anhydrous emulsions.

In a preferred embodiment, an antiperspirant composition comprises one or more active antiperspirant agents, such as, for example, aluminum halides, and aluminum hydroxyhalides, for example, aluminum chlorohydrate, and complexes or mixtures thereof with zirconyl oxyhalides and zirconyl hydroxyhalides, such as for example, aluminum-zirconium chlorohydrate, and the silicone elastomer of the present invention.

In a preferred embodiment, a skin care composition comprises silicone elastomer of the present invention, and optionally, further comprises a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, vitamin C and vitamin E, sunscreen or sunblock compounds, such as for example, titanium dioxide, oxybenzone sunscreens and p-aminobenzoic acid.

The personal care composition of the present invention may, optionally, further contain such know components as, for example, emollients, moisturizers, humectants, pigments, colorants, fragrances, biocides, preservatives, exfoliants, hormones, enzymes, medicinal compounds, anti-microbial agents, anti-fungal agents, vitamins, salts, electrolytes, alcohols, polyols, absorbing agents for ultraviolet radiation, botanical extracts, surfactants, silicone oils, organic oils, waxes, thickening agents such as, for example, fumed silica or hydrated silica, clays, such as, for example, bentonite, and organo-modified clays.

EXAMPLES

The following example illustrates the process of the present invention. It is illustrative and the claims are not to be construed as limited to the example.

Comparative Example 1

The silicone elastomer of Comparative Example 1 is made as described in, for example, U.S. Pat. No. 5,760,116, the disclosure of which is hereby incorporated by reference herein, by combining: (i) 2000 grams of 40,000 cStk divinyl siloxane of the average formula $M^{vi}{}_2 D_{900}$, wherein $M^{vi}$ and D are each defined as for formula (I) above; $R^4$ is ethenyl; and $R^5$, $R^6$, $R^7$ and $R^8$ are each methyl; and (ii) 9.1 grams of silylhydride functional resins of the average formula $((M^H)_2 Q)_4$, wherein $M^H$ and Q are each defined as for formula (II) above, $R^{13}$ is H and $R^{14}$ and $R^{15}$ are each methyl with 6000 grams of $D_5$ in a Drais® mixer. 0.4 grams of a platinum catalyst (5 ppm platinum level) was then added to the reactor. The contents of the reactor were then stirred and heated to 80° C. over 7 hours. The polymerized solid product, in the form of a fluffy white powder, was then removed from the reactor, diluted to 5.5 wt % solids with $D_5$ and subjected to high shear in a Sonolator homogenizer to produce a clear gel. 100 grams of the material was then placed into a metal beaker equipped with a paddle stirrer. 20 grams of water was slowly dripped in. After an initial cloudiness at a very low level of water addition, two phases—oil and water—were consistently observed. The results indicate that no emulsion was formed. (The polyether compound has been omitted.)

Example 2

The silicone elastomer of Example 2 is made by combining (i) 2000 grams of the divinyl siloxane described above in Example 1, (ii) 53.7 grams of silylhydride-functional resin of the average formula $((M^H)_2 Q)_4$, wherein: $M^H$ and Q are each defined as for formula (II) above, $R^{16}$ is H and $R^1$, $R^2$, $R^3$, $R^7$, $R^8$, $R^{13}$, $R^{14}$, $R^{15}$ and $R^{17}$ are each methyl, and (iii) 160 grams of allyl started, 550 molecular weight ("MW") ethylene oxide polyether with 6000 grams of $D_5$ in a Drais® mixer. The mixture was stirred and 0.82 grams (10 ppm platinum level) of platinum catalyst was added. The reaction was heated to 85° C. over 5 hours, and a gel was formed. The product was then diluted to about 4.07% elastomer solids content with $D_5$ and then subjected to high shear in a Sonolator® homogenizer for four passes at 4500 psi (0.00096 inch orifice) to generate a clear gel.

Example 3

The silicone elastomer of Example 3 is made by combining (i) 2000 grams of the divinyl siloxanes described above in Example 1, (ii) 21.4 grams of silylhydride-functional resin of the average formula $((M^H)_2 Q)_4$, wherein: $M^H$ and Q are each defined as for formula (II) above, $R^{16}$ is H and $R^1$, $R^2$, $R^3$, $R^7$, $R^8$, $R^{13}$, $R^{14}$ $R^{15}$ and $R^{17}$ are each methyl, and (iii) 160 grams of allyl started, 1800 MW ethylene oxide/propylene oxide polyether with 6000 grams of $D_5$ in a Drais® mixer. The mixture was stirred and 0.82 grams (10 ppm platinum level) of platinum catalyst was added. The reaction was heated to 85° C. over 7 hours, and a gel was formed. The product was then diluted to about 4.9% elastomer solids content with $D_5$ and then subjected to high shear in a Sonolator® homogenizer for four passes at 4500 psi (0.00096 inch orifice) to generate a clear gel.

Example 4

100 grams of the material from Example 2 was placed in a metal beaker equipped with a paddle stirrer. 20 grams of water was slowly added. As the water was added, a milky white cream was formed. No phase separation was observed, indicating the formation of an emulsion.

Example 5

100 grams of the material from Example 3 was placed in a metal beaker equipped with a paddle stirrer. 20 grams of water was slowly added. As the water was added, a milky white cream was formed. No phase separation was observed, indicating the formation of an emulsion.

Example 6

The silicone elastomer of Example 6 is made by combining (i) 119 grams of the divinyl siloxanes described above in Example 1, (ii) 2.3 grams of silylhydride-functional resin of the average formula $((M^H)_2 Q)_4$, wherein: $M^H$ and Q are each defined as for formula (II) above, $R^{16}$ is H and $R^1$, $R^2$, $R^3$, $R^7$, $R^8$, $R^{13}$, $R^{14}$, $R^{15}$ and $R^{17}$ are each methyl, and (iii) 23.8 grams of allyl started, 550 MW ethylene oxide polyether with 357 grams of $D_5$ and 75 grams of isopropyl alcohol in a dough mixer. The mixture was stirred and 0.025 grams (5 ppm platinum level) of platinum catalyst was added. The reaction was heated to 85° C. over 7 hours, and a gel was formed. The isopropyl alcohol was removed by distillation. The product was then diluted to about 6.0% elastomer solids content with $D_5$ and then subjected to high shear in a Gaulin® homogenizer for five passes at 8000 psi to generate a clear gel.

Example 7

An anhydrous antiperspirant was formulated using the polyether functionalized elastomer as the sole gellant to stabilize the antiperspirant actives. The resultant formula was a thick cream with excellent smooth, dry feel. The formula did not leave any visible residue.

The antiperspirant was made by adding 25 grams of aluminum-zirconium chlorohydrex-gly ("ZAG") to 75 grams of the polyether elastomer of Example 6 and mixing thoroughly at moderate to high speed until smooth (approximately 5 minutes). The order of addition or the mixing speed is not critical as long as the mixture is homogenous and contains no large agglomerates.

Example 8

A water-in-oil silicone emulsion using the polyether functionalized elastomer as the sole emulsifier was formulated. The resultant formula was a thick cream with good sensory characteristics.

The emulsion was made by preparing the oil phase and water phase separately. The oil phase was prepared by adding 19.5 grams of $D_5$ to 46.8 grams of the polyether elastomer of Example 6 and mixing thoroughly. The water phase, 33.7 grams of a 1% NaCl solution, was slowly added to the oil phase such that the water phase is completely "taken up" or "absorbed" by the oil phase. The resultant formula was a thick cream.

Example 9

A water-in-silicone emulsion was formulated using the polyether functionalized elastomer in conjunction with another water-in-silicone elastomer. The resultant formula was light and non-greasy with a smooth and powdery feel.

The emulsion was made by preparing the oil phase and water phase separately. The oil phase was prepared by adding 3.8 grams of $D_5$, 3.9 grams of dimethicone and 4.4 grams of cyclopentasiloxane and dimethicone copolyol to 19.3 grams of the polyether elastomer of Example 6 and mixing thoroughly. The water phase, 68.6 grams of a 1% NaCl solution, was slowly added to the oil phase such that the water phase is completely "taken up" or "absorbed" by the oil phase. The resultant formula was a thick cream.

Example 10

The silicone elastomer of Example 10 is made by combining (i) 1500 grams of divinyl siloxane like that described above in Example 1 except it has a viscosity of 36,000 Costco, (ii) 46.5 grams of silylhydride-functional resin of the average formula $M^H{}_2Q_4$, wherein: $M^H$ and Q are each defined as for formula (II) above, $R^{16}$ is H and $R^1$, $R^2$, $R^3$, $R^7$, $R^8$, $R^{13}$, $R^{14}$, $R^{15}$ and $R^{17}$ are each methyl, (iii) 23.6 grams of divinyl siloxane like that in (i) above except it has a viscosity of 22 cStk, and (iv) 381 grams of allyl started, 1800 MW ethylene oxide polyether with 5853 grams of $D_5$ and 75 grams of isopropyl alcohol in a Drais® mixer. The mixture was stirred and 0.78 grams (10 ppm platinum level) of platinum catalyst was added. The reaction was heated to 95° C. over 5 hours, and a gel was formed. The product was then diluted to about 7.5% elastomer solids content with $D_5$ and then subjected to high shear in a Gaulin® homogenizer for five passes at 8000 psi to generate a clear gel.

Example 11

An oil-in-water emulsion was formed using the polyether functionalized silicone elastomer. 20.0 grams of the elastomer from Example 10, 5.0 grams of isopropyl myristate and 1.0 gram of Germaben II were mixed together. 20.0 grams of carbopol (2% aqueous solution) were added to the batch under high shear mixing. 2.0 grams of propylene glycol and 51.8 grams of water were added to the batch and mixed thoroughly, and the batch was then neutralized with 0.2 grams of triethanolamine ("TEA"), forming an oil-in-water emulsion.

Example 12

An oil-in-water sunscreen was formed using the polyether functionalized silicone elastomer. 20.0 grams of the elastomer from Example 10, 7.5 grams of octyl methoxycinnamate, 10.0 grams of octocrylene and 1.0 gram of Germaben II were mixed together. 20.0 grams of carbopol (2% aqueous solution) were added to the batch under homogenization. 2.0 grams of propylene glycol and 39.3 grams of water were added to the batch and mixed thoroughly, and the batch was then neutralized with 0.2 grams of TEA, forming an oil-in-water sunscreen.

Example 13

A water-in-oil emulsion was formed using the polyether functionalized silicone elastomer. 8.0 grams of octyldodecyl neopentanoate and 60.0 grams of the elastomer of Example 10 were mixed together, and 1.0 gram of Germaben II was added (oil phase). 30.0 grams of water and 1.0 gram of a 1% NaCl solution were mixed together in a separate container (water phase). The water phase was slowly added to the oil phase, and a water-in-oil emulsion was formed.

Example 14

A stick antiperspirant was formulated using the polyether functionalized silicone elastomer. 30.0 grams of cyclopentasiloxane and 20.0 grams of the elastomer of Example 10 were well mixed and then heated to 75° C. 19.0 grams of stearyl alcohol, 3.0 grams of hydrogenated castor oil and 2.0 grams of glyceryl stearate and PEG 100 stearate were added. 4.0 grams of talc and 22.0 grams of ZAG were added to the batch and mixed. The mixture was cooled to 55° C. and poured into molds to form stick antiperspirant.

Example 15

An anhydrous antiperspirant was formulated using the polyether functionalized silicone elastomer. 33.0 grams of cyclopentasiloxane, 5.0 phenyl trimethicone, and 35.0 grams of the elastomer of Example 10 were mixed together. 2.0 grams of ethanol and 25.0 grams of ZAG were added to the batch. Anhydrous roll on antiperspirant was formed.

Example 16

An antiperspirant emulsion was formulated using the polyether functionalized silicone elastomer. 17.0 grams of dimethicone (100 ctsk) and 43.0 grams of the elastomer of Example 10 were mixed together. 20.0 grams of water and 20.0 grams of ZAG were mixed together in a separate container, and the mixture was then added to the batch. An antiperspirant emulsion was formed.

Example 17

Powder eyeshadow was formulated using the polyether functionalized silicone elastomer. 37.0 grams of talc, 30.0 grams of mica, 5.0 grams of bismuth oxychloride, 3.0 grams of zinc stearate, 5.0 grams of boron nitride, 0.2 grams of methylparaben, 0.1 grams of propylparaben, and 12.2 grams of iron oxides (red, yellow and black) were combined and mixed until homogenous. 4.0 grams of the elastomer of Example 10 and 3.5 grams of dimethicone (5 ctsk) were mixed together in a separate container, and added to the batch. The material was pressed into a suitable container to form a powder eyeshadow.

Example 18

A lipstick was formulated using the polyether functionalized silicone elastomer. 34.3 grams of petrolatum, 6.0 grams of mineral oil, 4.0 grams of candelilla wax, 3.0 grams of carnauba wax, 10.0 grams of microcrystalline wax and 6.0 grams of beeswax were melted together. 3.0 grams of phenyl trimethicone and 3.0 grams of the elastomer of Example 10 were mixed together and added to the batch to form a mixture. 15.7 grams of castor oil and 6.0 grams of D&C red No. 7 Calcium lake were combined and passed through a roller mill, and then added to the above mixture. 5.0 grams of mica and iron oxide and 4.0 grams of mica were added to the batch and mixed together. A lipstick was formed.

Examples 19 to 28

The following hair care formulations are made using the polyether substituted silicone elastomer of the invention. They are combined in the proportions shown in the tables below.

Example 19—Shampoo

| Ingredient | Amount (% by weight) |
| --- | --- |
| Ammonium lauryl sulfate | 24.00 |
| Ammonium laureth sulfate | 14.30 |
| Cocamidopropyl betaine | 11.43 |
| Lauramid DEA | 2.00 |
| Cocamid MEA | 2.50 |
| Polyether elastomer of Example 10 | 0.50 |
| Cyclopentasiloxane | 5.00 |
| Dimethicone copolyol | 1.00 |
| Polyquaternium-10 | 0.50 |
| Preservative | 0.20 |
| Fragrance | 0.50 |
| Deionized water | q.s. 100% |
| Sodium chloride | q.s. n |

Example 20—Conditioner

| Ingredient | Amount (% by weight) |
| --- | --- |
| Ceteareth-20 | 0.50 |
| Steareth-20 | 0.50 |
| Stearyl Alcohol | 2.00 |
| Stearamidopropyl dimethylamine | 0.80 |
| Dicetyldimonium chloride | 1.50 |
| Polyether elastomer of Example 10 | 0.50 |
| Cyclopentasiloxane | 5.00 |
| Dimethicone | 0.50 |
| Preservative | 0.20 |
| Fragrance | 0.50 |
| Deionized water | q.s. 100% |

Example 21—Fixative Lotion

| Ingredient | Amount (% by weight) |
| --- | --- |
| Polyether elastomer of Example 10 | 2.50 |
| Cyclopentasiloxane | 42.50 |
| SDA-40 alcohol | 54.50 |
| Fragrance | 0.50 |

Example 22—Fixative Gel

| Ingredient | Amount (% by weight) |
| --- | --- |
| Polyether elastomer of Example 10 | 4.00 |
| Cyclopentasiloxane | 41.00 |
| SDA-40 alcohol | 54.50 |
| Fragrance | 0.50 |

Example 23—Fixative Spritz

| Ingredient | Amount (% by weight) |
| --- | --- |
| Polyether elastomer of Example 10 | 1.00 |
| Cyclopentasiloxane | 44.00 |
| SDA-40 alcohol | 54.50 |
| Fragrance | 0.50 |

Example 24—Fixative Spray

| Ingredient | Amount (% by weight) |
| --- | --- |
| Polyether elastomer of Example 10 | 1.00 |
| Cyclopentasiloxane | 3.00 |
| SDA-40 alcohol | 54.50 |
| Fragrance | 0.50 |
| Propellant 152a | 41.00 |

Example 25—Fixative with Secondary Resin

| Ingredient | Amount (% by weight) |
| --- | --- |
| Polyether elastomer of Example 10 | 2.50 |
| Cyclopentasiloxane | 25.00 |
| SDA-40 alcohol | 54.50 |
| Octylacrylamide/acrylates/butami | 2.00 |
| 1-Aminomethyl propanol | q.s. pH |
| Fragrance | 0.50 |
| Deionized water | q.s. 100% |

Example 26—Mousse for Hair

| Ingredient | Amount (% by weight) |
| --- | --- |
| Polyether elastomer of Example 10 | 2.50 |
| Cyclopentasiloxane | 4.00 |
| Nonoxynol-15 | 0.60 |
| Nonoxynol-20 | 0.60 |
| Fragrance | 0.50 |
| Propellant 152a | 8.00 |
| Preservative | 0.20 |
| Deionized water | q.s. 100% |

Example 27—After-color Conditioner

| Ingredient | Amount (% by weight) |
| --- | --- |
| Ceteareth-20 | 0.50 |
| Steareth-20 | 0.50 |
| Stearyl Alcohol | 2.00 |
| Stearamidopropyl dimethylamine | 0.80 |
| Dicetyldimonium chloride | 1.50 |
| Polyether elastomer of Example 10 | 0.50 |
| Cyclopentasiloxane | 5.00 |
| Amodimethicone | 1.50 |
| Preservative | 0.20 |
| Fragrance | 0.50 |
| Deionized water | q.s. 100% |

Example 28—Cream Hair Dye

| Ingredient | Amount (% by weight) |
| --- | --- |
| Cetyl alcohol | 4.50 |
| Stearyl Alcohol | 4.50 |
| Ceteareth-20 | 0.50 |
| Steareth-20 | 0.50 |
| Anthraquinone dye | 1.00 |
| Polyether elastomer of Example 10 | 0.50 |

-continued

| Ingredient | Amount (% by weight) |
| --- | --- |
| Cyclopentasiloxane | 5.00 |
| Aqueous ammonium hydroxide | q.s. pH = 9 |
| Deionized water | q.s. 100% |

Having described the invention, we claim:

1. A silicone composition, comprising: a liquid medium, said liquid medium comprising an organic liquid; and a silicone elastomer dispersed in the liquid medium, said elastomer comprising the cross-linked hydrosilylation reaction product of (i) an alkenyl functional silicone compound; (ii) a silylhydride functional silicone compound; and (iii) one or more allyl started, hydrogen, alkyl, aryl or acyl terminated polyether compounds.

2. The silicone composition of claim 1, wherein the composition is subjected to shear force to break the silicone elastomer into particles.

3. The silicone composition of claim 1, wherein the composition comprises, based on 100 parts by weight of the composition, from 1 part by weight to 99 parts by weight of the liquid medium, from 1 part by weight to 99 parts by weight of the silicone elastomer.

4. The silicone composition of claim 1, wherein the liquid medium comprises an organic liquid and a silicone fluid that is miscible with the organic liquid.

* * * * *